US00PP11523P

United States Patent [19]

Groves

[11] Patent Number: Plant 11,523

[45] Date of Patent: Sep. 26, 2000

[54] NEOREGELIA PLANT NAMED 'LILA'

[76] Inventor: Grant Groves, 9940 Black Bear La., Winter Garden, Fla. 34787

[21] Appl. No.: 09/128,776

[22] Filed: Aug. 4, 1998

[51] Int. Cl.[7] ..... A01H 5/00

[52] U.S. Cl. ..... Plt./370

[58] Field of Search ..... Plt./370

*Primary Examiner*—Howard J. Locker
*Assistant Examiner*—Wendy A Baker
*Attorney, Agent, or Firm*—Rothwell, Figg, Ernst & Kurz

[57] ABSTRACT

A new and distinct cultivar of Neoregelia is provided. It is a medium size Neoregelia plant, suitable for production in 12.5 to 15 cm pots. 'Lila' is a relatively low spreading rosette, full and symmetrical with numerous, closely overlapping, wide, relatively short and flat, glossy leaves. Several bright red-purple upper leaves provide the dominant plant color.

1 Drawing Sheet

SUMMARY OF THE INVENTION

This invention relates to a new and distinct Neoregelia cultivar characterized by the following combination of repeatedly observed traits:

1. Medium size,
2. relatively low spreading rosette,
3. full and symmetrical growth habit,
4. numerous, wide and relatively flat, closely overlapping, glossy leaves,
5. top leaves bright red-purple, bottom leaves green, and primarily selected for these characteristics from the progeny of the cross stated below in a cultivated area near Orlando, Fla.

ORIGIN AND ASEXUAL REPRODUCTION

The new cultivar is a product of a planned breeding program carried out at Tropical Arts, Inc. near Orlando, Fla. The female parent was a hybrid Neoregelia 'Pink Sensation' obtained in the program. The male parent was a hybrid Neoregelia 'Passion' × Neoregelia 'Grace', which also resulted from this program. Patent applications have not been filed for any of the parent cultivars. The cross was made in 1980 and the plant was selected in 1983. It has been asexually reproduced by tissue culture in the vicinity of Altha, Fla. since 1995 with the characteristics stated, found to be maintained through successive generations.

This new cultivar has been identified as Neoregelia 'Lila'.

BRIEF DESCRIPTION OF THE PHOTOGRAPHS

The accompanying photographs show as nearly true as it is reasonably possible, in a color illustration of this character, typical specimens of the plant parts of the new cultivar. The plant of 'Lila' was approximately one year from planting an offshoot in a 15 cm pot. Colors in the photographs may appear different from actual colors due to light reflectance.

In the photographs:

DETAILED DESCRIPTION OF THE NEW CULTIVAR

Figure 1:
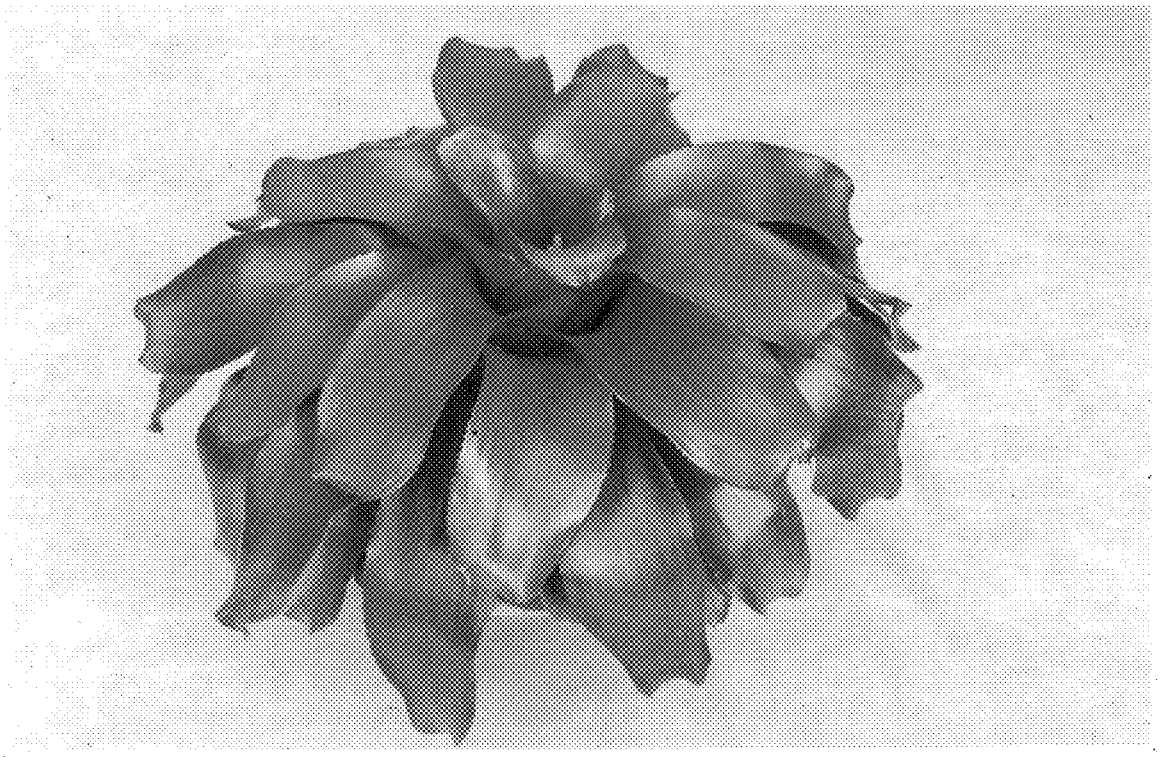
FIG. 1 depicts the whole plant.
Figure 2:
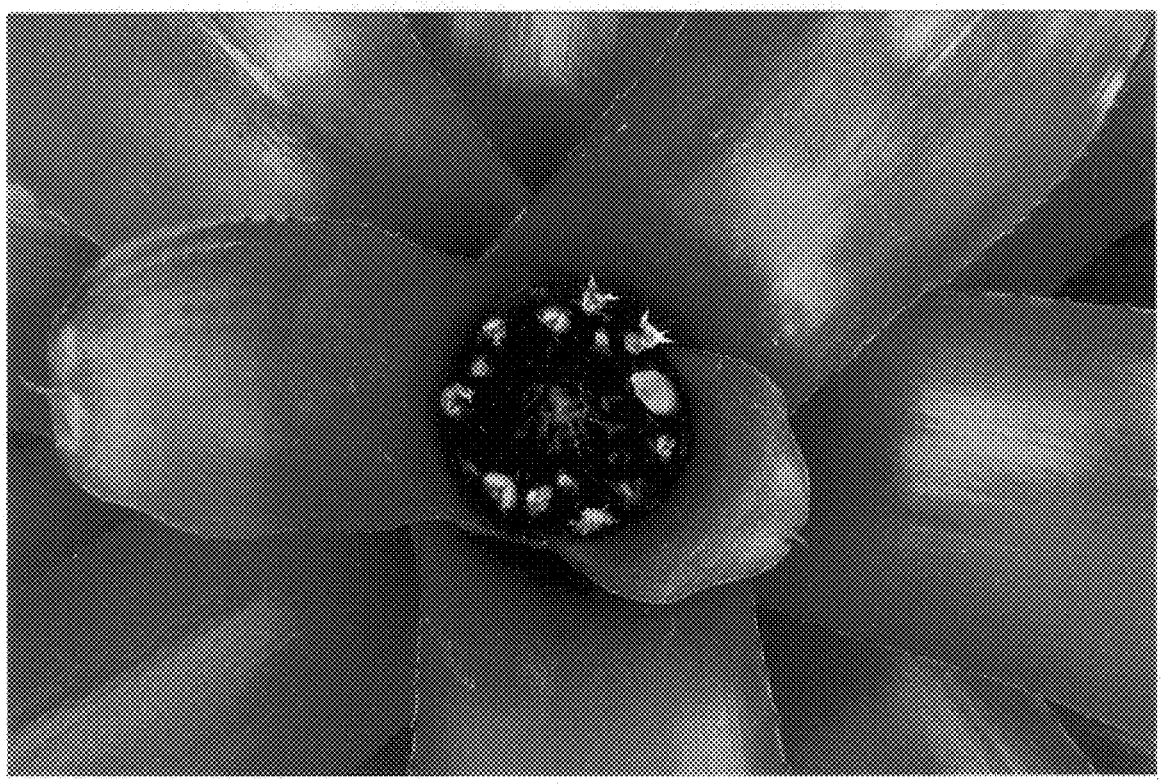
FIG. 2 illustrates the inflorescence.

The following observations and measurements describe plants grown near Orlando, Fla. under shadehouse conditions. These observations and measurements were recorded near Altha, Fla. in February, 1998 from mature flowering plants in 15 cm pots, about a year from planting offshoots. Color values were determined on Feb. 5, 1998 under a natural, indirect light of approximately 700–1000 foot-candles. Color references are made to the R.H.S. Colour Chart, except where general color terms of ordinary significance are used. Multiple color designations have been used to describe in greater detail the array of colors present.

'Lila' has not been observed under all possible environmental conditions. The phenotype may vary depending on environment and horticultural practices, such as temperature, light intensity, day length, fertilization, propagation method, etc., as well as developmental phase, without any change in genotype.

Botanical classification: Neoregelia hybrid cultivar Lila.

Parentage:

*Female parent.*—Neoregelia'Pink Sensation' (not patented).

*Male parent.*—Neoregelia 'Passion' (not patented) × Neoregelia 'Grace' (not patented).

Propagation: Plant tissue culture, offshoots.

Plant descriptions:

*Growth habit.*—Medium size; symmetrical, relatively low spreading rosette, full, with very short stem and closely overlapping leaves.

*Height.*—From soil level to top of plant: 17.0–20.5 cm.

*Width.*—42.0–45.0 cm.

*Number of leaves.*—34–46.

Leaves:

*Shape.*—Leaf blades lingulate, recurved, broadly rounded and apiculate; margins edged with spines. Two to three of the three upper leaves forming the central tank are usually very short and vertical or oblique; the fourth leaf form the top, situated outside the central tank, is usually approximately horizontal. Progressing down the stem leaves become longer and more recurved.

*Size.*—The width was measured at the widest point of the free part of the leaf blade. The fourth leaf from the top: 15.5–17.6 cm long, 6.5–7.4 cm wide; length: width ratio 2.2–2.7:1. The longest leaf: 27.5–32.0 cm long; 6.8–7.4 cm wide; length: width ratio 3.7–4.7:1.

*Texture.*—Adaxial: finely ribbed, glossy. Abaxial: smooth, glossy.

*Veins.*—Numerous, roughly equal-sized, parallel veins run the length of the blade converging at its tip. They appear as very fine ribs on the adaxial surface.

Color:

*Adaxial.*—The top 12–16 leaves are bright red-purple (varying between 64A, 58A, 59C, 61A and combinations thereof) and give the plant its dominant color. The greyed-purple coloration of their margins (varying between 187B, 187A, 183A, 183B and combinations thereof) is especially pronounced in the distal portions and sometimes, particularly on lower red-purple leaves, mainly on the spines. Near leaf tip where veins converge, dark green to greyed-purple streaks merge to sometimes form a small almost solid color zone. It occurs on the fourth and lower leaves and it tends to be more greyed-purple on the higher leaves and greener on the lower leaves. Foliage of the lower portion of the plant is predominantly green—147A (yellow-green) or darker with various amounts of red-purple, similar to or sometimes lighter (similar to 59D) than the color of upper leaves. Red-purple frequently occurs in areas near the leaf bases mostly covered by higher leaves and in red-purple longitudinal streaks near the tip, proximal to the green zone of converging veins. Occasionally red-purple streaks run along entire length of a leaf. The margin of the green leaves is greyed-purple (varying between 187B, 187A, 183A, 183B and combinations thereof). Sometimes the greyed-purple coloration is limited to the spines. The lowermost aging leaves tend to be lighter and more yellow with some areas resembling a color varying from 144A to 144C. A few leaves at the transition between red-purple and green leaves may have both colors diffused through most of the leaf blade.

*Abaxial.*—The red-purple color of the uppermost leaves is less bright than on the adaxial side, most similar to a color between 64A, 58A, 70A and 71B. The lower red-purple leaves appear more grayish and darker than on the adaxial side. The green zones near tips are brighter than on the adaxial side (most similar to 146A with some resemblance to 147A). The abaxial side of green leaves is lighter and more yellow than the adaxial side (146A) and the red-purple markings are lighter.

Inflorescence:

*Arrangement.*—Simple, many-flowered, condensed rosette 4.3–4.6 cm in diameter, deeply sunken in the central tank.

Botanical flower:

*Shape and size.*—Epigynous, tubular, approximately 4.7–5.1 cm long and 0.6–0.9 cm wide when fully open. Three sepals and three petals become free at the summit of an inferior ovary. The length measurements of petals and sepals refer to their free part. Petals extend approximately 1.0–1.5 cm past sepals and open slightly, not fully exposing pistil and stamens, which extend to almost the same height, much below petals tips. Sepals between oblanceolate and lingulate, approximately 2.7–2.9 cm long and 0.8–1.0 cm wide; tip between acuminate and aristate. Petals between oblanceolate and lingulate, approximately 3.9–4.4 cm long and 0.6–0.7 cm wide; tip between acute and acuminate. Pistil: Ovary oblong, approximately 1.0–1.3 cm long and 0.5–0.6 cm in diameter. Style approximately 2.0–2.3 cm long; stigma approximately 4.0–6.0 mm long and 1 mm wide. Stamens: Approximately 2.3–2.6 cm long. Filaments approximately 2.0–2.2 cm long; anthers approximately 4.5–5.5 mm long and 1 mm wide.

*Color.*—Sepals (abaxial): Most of distal zone including tip 144A (yellow-green). Proximally becomes gradually lighter through 144B, 144C, 144D, 157C to 157D (green-white) at the summit with ovary. Margin and veins translucent. Petals: Proximal up to 2.5 cm of petals forming a tube darker than 155D (white), but lighter than 156D (greyed-white), both adaxial and abaxial. Distal approximately 1.5 cm, where petals separate: adaxial 86A-D with the central band darkest (86A) and margin lightest (85D); abaxial 85A-D (all violet), with the central band lightest. Pistil: Style and stigma darker than 155D (white), but lighter than 156D (greyed-white). Stamens: Filaments darker than 155D (white), but lighter than 156D (greyed-white). Anthers between 158A, 161C, 161D, 162C and 162D. Pollen yellow-white.

Fruit: Spontaneous seed and fruit production not observed.

Roots: Numerous, long, thin, hard main roots, cream to brown. Lateral roots relatively few, thin, cream to brown.

Flowering: Individual flower lasts for one day; up to three flowers appear simultaneously. Flowers continue to appear for a period of approximately 2 months.

Disease and insect resistance: Plants of 'Lila' which are grown in commercial bromeliad greenhouses have not shown any unusual susceptibility to pathogens or insects common to Neoregelia.

Comparison with the known cultivars: The new cultivar can be compared to the known Neoregelia cultivars: 'Grace' (not patented) and 'Charlotte' (not patented).

The comparisons were made near Altha, Fla.on plants grown under similar conditions in a shadehouse near Orlando Fla.

'Lila' is distinguished from both cultivars by its distinct bright red-purple color; fuller growth habit and wider, closer overlapping, more glossy leaves.

'Lila' is further distinguished from 'Grace' by its more recurved leaves.

'Lila' is further distinguished from 'Charlotte' by its smaller size and shorter leaves.

I claim:

1. A new and distinct cultivar of Neoregelia plant named 'Lila', substantially as described and illustrated herein, characterized as to novelty by its medium size; relatively low spreading, full, symmetrical rosette growth habit; numerous, wide, closely overlapping, glossy leaves; bright red-purple color of dominant top leaves and green with red-purple color of bottom leaves.

* * * * *